United States Patent [19]
Abe et al.

[11] 4,235,782
[45] Nov. 25, 1980

[54] PERFLUORO(4-METHYL-2-OXABICY-CLO[4.4.0]DECANE) AND METHOD FOR MANUFACTURE THEREOF

[75] Inventors: Takashi Abe; Shunji Nagase, both of Nagoya, Japan

[73] Assignee: Agency of Industrial Science & Technology, Ministry of International Trade & Industry, Tokyo, Japan

[21] Appl. No.: 58,628

[22] Filed: Jul. 18, 1979

[30] Foreign Application Priority Data

Jul. 21, 1978 [JP] Japan ................................ 53-89846

[51] Int. Cl.$^3$ .......................................... C07D 311/00
[52] U.S. Cl. .............................. 260/345.2; 204/59 F; 252/364
[58] Field of Search ...................................... 260/345.2

[56] References Cited

U.S. PATENT DOCUMENTS 2,594,272   4/1952   Kauck et al. ..................... 260/345.1
2,644,823   7/1953   Kauck et al. ..................... 260/345.1

FOREIGN PATENT DOCUMENTS 1069639   11/1959   Fed. Rep. of Germany ......... 204/59 F
123658    of 1975   Japan ................................ 260/346.11

OTHER PUBLICATIONS

Bailey et al., Tetrahedron Letters, 11, 869 (1975).

Primary Examiner—Nicky Chan
Attorney, Agent, or Firm—Kurt Kelman

[57] ABSTRACT

Perfluoro(4-methyl-2-oxabicyclo[4.4.0]decane) is a novel compound and this novel compound is manufactured by the electrolytic fluorination of 2-methyl-3-cyclopropionic acid or a derivative thereof in hydrogen fluoride.

1 Claim, 1 Drawing Figure

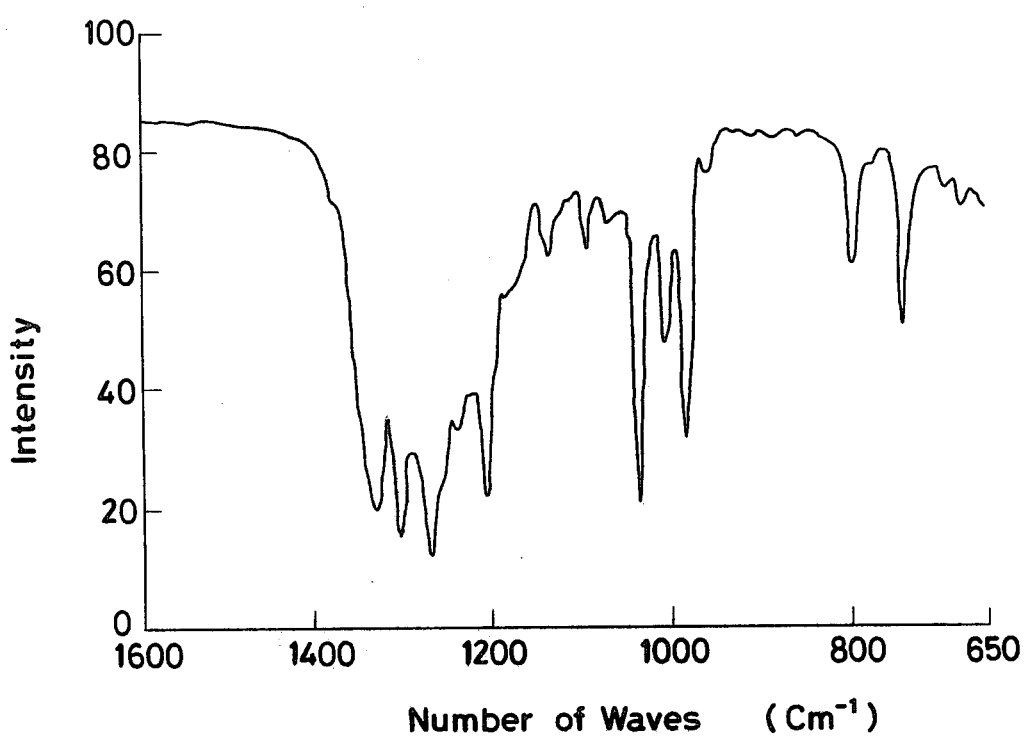

PERFLUORO(4-METHYL-2-OXABICYCLO[4.4.0]-DECANE) AND METHOD FOR MANUFACTURE THEREOF

BACKGROUND OF THE INVENTION

This invention relates to perfluoro(4-methyl-2-oxabicyclo[4.4.0]decane), a novel compound, and to a method for the manufacture thereof.

Generally, perfluorocyclic ethers are thermally and chemically stable and, therefore, are widely used as inactive solvents etc. Recently, the appreciation of the fact that these ethers have an exceptionally high capacity for dissolving oxygen and carbon dioxide has led to development of a use wherein they serve as carriers for artificial blood in the field of life science.

Heretofore, monocyclic perfluoro-ether compounds have been manufactured by the electrolytic fluorination of monocyclic ethers (U.S. Pat. No. 2,594,272 and British Pat. No. 672,720), by the electrolytic fluorination of chain type carboxylic acids and derivatives thereof (U.S. Pat. No. 2,644,823, British Pat. No. 718,318. German Pat. No. 1,069,639, French Pat. No. 1,636,296) or by the electrolytic fluorination of alcohols and aldehydes (Japanese Pat. No. 882,005, Japanese Patent Laid-open Publication Sho 50(1975)-123658 and Japanese Pat. No. 822,539), for example.

Perfluorobicyclo-ether compounds have been synthesized by the fluorination of benzofuran with cobaltic trifluoride (J. Bailey, R. G. Plevey and J. C. Tatlow, "Tetrahedron Letters", No. 11, 869 (1975)), for example.

An object of the present invention is to provide perfluoro(4-methyl-2-oxabicyclo[4.4.0]decane), a novel perfluorobicyclo-ether compound which is thermally and chemically stable and possesses outstanding properties for use as an inactive solvent.

Another object of the present invention is to provide a method for the electrolytic manufacture of perfluoro(4-methyl-2-oxabicyclo[4.4.0]decane), a novel perfluorobicyclo-ether compound which is thermally and chemically stable and possesses outstanding properties for use as an inactive solvent.

SUMMARY OF THE INVENTION

The objects described above are attained by this invention which derives from the discovery that when 2-methyl-3-cyclohexylpropionic acid or a derivative thereof represented by the generic formula:

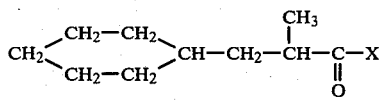

(wherein, X denotes a hydroxyl group, a halogen atom, a methoxy group, ethoxy group or an amino group) is subjected to electrolytic fluorination, there ensue fluorination and cyclization resulting in a reaction product containing, as a principal component, perfluoro(4-methyl-2-oxabicyclo[4.4.0]decane), a novel perfluorocyclo-ether compound.

BRIEF EXPLANATION OF THE DRAWING

The drawing represents an infrared absorption spectrum obtained of the perfluoro(4-methyl-2-oxabicyclo[4.4.0]decane) of this invention.

DETAILED DESCRIPTION OF THE PREFERRED EMBODIMENTS

This invention is directed to providing perfluoro(4-methyl-2-oxabicyclo[4.4.0]decane), a novel compound having the structural formula:

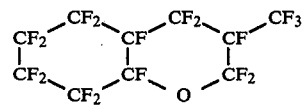

and, further, to providing a method for the manufacture of perfluoro(4-methyl-2-oxabicyclo[4.4.0]decane), which method is characterized by subjecting 2-methyl-3-cyclohexylpropionic acid or a derivative thereof represented by the generic formula:

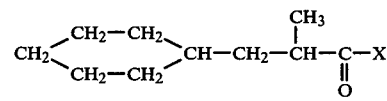

(wherein, X denotes a hydroxyl group, a halogen atom or a methoxy, ethoxy or amino group) to electrolytic fluorination in hydrogen fluoride for thereby causing the reactant to undergo simultaneous fluorination and cyclization.

The perfluoro(4-methyl-2-oxabicyclo[4.4.0]decane) produced by the present invention possesses a boiling point of 127.2° to 127.5° C., a refractive index of $n_D^{20}$ 1.3012 and a density of $d_D^{20}$ 1.8655 and exhibits the infrared absorption spectrum illustrated in the accompanying drawing.

The raw materials to be used for the manufacture of perfluoro(4-methyl-2-oxabicyclo[4.4.0]decane) are hydrogen fluoride and 2-methyl-3-cyclohexylpropionic acid or a derivative thereof. Specific examples of the derivatives which are used for this purpose are as follows.

Methyl ester of 2-methyl-3-cyclohexylpropionic acid
2-Methyl-3-cyclohexylpropionyl chloride
2-Methyl-3-cyclohexylpropionamide The electrolysis is generally carried out by having the 2-methyl-3-cyclohexylpropionic acid or derivative thereof dissolved in hydrogen fluoride. The 2-methyl-3-cyclohexylpropionic acid or derivative thereof is desired to be present in a concentration in the range of from 0.1 to 0.3 mol per 1 liter of hydrogen fluoride.

This electrolysis is effectively carried out in any of the horizontal and vertical tanks which are generally used for the purpose of electrolytic fluorination.

In due consideration of the chemical actions produced by the electrolyte and the reaction product involved, the electrolytic cell is desired to be made of a material resistant to corrosion. Typical examples of such material include Monel metal and mild steel. As regards the electrodes, it is advantageous to use an anode made of nickel and a cathode made of nickel or iron, for example. Although the optimum reaction conditions are variable with the kinds of raw materials selected, the composition and concentration of the electrolyte to be used and the distance between the electrodes, it is generally important that the voltage of the electrolytic bath, the temperature of the bath and the anodic current density should be set so as to fall within the respective ranges shown below.

Temperature of electrolytic bath—3° C. to 8° C.

Distance between the electrodes—1.7 mm to 3.0 mm

Voltage of electrolytic bath—When the electrodes are separated by the distance indicated above, it is advantageous to begin the electrolysis at a minimum of 5 V and to continue it to a maximum of 8 V.

Anodic current density—2.0 A/dm$^2$ to 4.0 A/dm$^2$

When the electrolysis is carried out under the conditions indicated above, perfluoro(4-methyl-2-oxabicyclo[4.4.0]decane) is produced in conjunction with oxygen difluoride, carbonyl fluoride, etc.

The greater part of the perfluoro(4-methyl-2-oxabicyclo[4.4.0]decane) which is aimed at by the electrolysis remains in conjunction with other fluorocarbons in the electrolytic cell, forming one phase separated from hydrogen fluoride which forms the other phase. After completion of the electrolytic fluorination, the phase of the fluorocarbons containing the desired perfluoro(4-methyl-2-oxabicyclo[4.4.0]decane) is drawn off. In the course of the electrolytic fluorination, part of the formed perfluoro(4-methyl-2-oxabicyclo[4.4.0]decane) is entrained by the formed gas. The entrained part of the product can be captured in a liquefied form in conjunction with fluorocarbons having not less than five carbon atoms when the formed gas is passed first through a bed of pellets of sodium fluoride and subsequently through a trap cooled with dry ice and acetone.

The mixture of the product of this invention, perfluoro(4-methyl-2-oxabicyclo[4.4.0]decane), with the fluorocarbons mentioned above can be separated as by means of fractional distillation or fractional gas chromatography. Since oxygen difluoride and carbonyl fluoride cannot be condensed by the aforementioned trap, they are removed by causing the formed gas to pass through a gas scrubber bottle (containing a mixed aqueous solution of potassium sulfite and potassium hydroxide), for example.

According to the present invention, the novel compound perfluoro(4-methyl-2-oxabicyclo[4.4.0]decane) can be obtained very easily. This product is thermally and chemically stable and possesses a high capacity for the dissolution of oxygen and carbon dioxide. Thus, it is highly useful as an inactive solvent, a carrier for artificial blood (for transfusion of oxygen), etc.

EXAMPLE 1

As an electrolytic cell, there was used a vertical, cylindrical container made of Monel metal, possessing an inner volume of 1 liter, containing therein eight anodes of nickel and nine cathodes of nickel arranged alternately and spaced by a fixed distance of 1.7 to 2.0 mm, having an effective anodic surface area of 9.2 dm$^2$ and provided in the upper section thereof with a reflux condenser. The electrolytic cell was filled with 1 liter of hydrogen fluoride, which was subjected to preliminary electrolysis for removal of traces of impurities (water and sulfuric acid). Then, 0.184 mol of methyl ester of 2-methyl-3-cyclohexylpropionic acid was dissolved in the hydrogen fluoride. With helium gas bubbled up the reactant mixture via the lower end of the container at a flow rate of 100 ml/min., the reactant mixture was electrolyzed for 229 Ahrs under the conditions of 3.5 A/dm$^2$ of anodic current density, 5.5 to 6.5 V of voltage and 5° to 6° C. of bath temperature until the electrolytic voltage reached 8.0 V.

After the completion of the electrolysis, the cock at the bottom of the electrolytic cell was opened to discharge 49.3 g of high-boiling fluorocarbons. When the fluorocarbons were freed from a trace of the residual hydrogen fluoride by addition of pellets of Molecular Sieve, 4A, and then analyzed by gas chromatography (with He as the carrier and 1,6-bis-(1,1,12-trihydroperfluorododecyloxy) hexane as the liquid phase), there was obtained 11.3 g of a colorless, transparent compound having a boiling point of 127.2° to 127.5° C. Upon analysis by infrared absorption spectroscopy, $^{19}$F nuclear magnetic resonance spectroscopy and mass spectroscopy, this compound was identified to be perfluoro(4-methyl-2-oxabicyclo[4.4.0]decane). At this time, as a corresponding perfluorocarboxylic fluoride, there was simultaneously obtained 11.2 g of perfluoro(2-methyl-3-cyclohexylpropionyl fluoride). When the formed gas was passed through a bed of sodium fluoride pellets and thereafter led to a trap cooled with dry ice and acetone, there was obtained 5.1 g of a mixture of fluorocarbons. When this mixture was similarly analyzed by gas chromatography, there was obtained 0.6 g of a colorless, transparent compound having a boiling point of 127.2° to 127.5° C. Upon analysis by the same methods as described above, it was identified to be perfluoro(4-methyl-2-oxabicyclo[4.4.0]decane). The two portions of the product, put together, were found by calculation to represent 13.4% of yield.

EXAMPLE 2

In the same electrolytic cell as used in Example 1, the electrolytic fluorination was carried out under the same reaction conditions by following the same procedure as in Example 1, except that 2-methyl-3-cyclohexylpropionyl chloride (0.150 mol) was used for 170 Ahrs until the electrolytic voltage reached 8.0 V.

After the completion of the electrolysis, the drain cock at the bottom of the electrolytic cell was opened to discharge 35.3 g of a mixture of fluorocarbons. Within the cooled trap, there was obtained 3.1 g of a mixture of fluorocarbons. These mixtures were put together and subjected to the same treatment and analysis as involved in Example 1. Consequently, there was obtained 7.1 g (9.9% of yield) of a product identified to be perfluoro(4-methyl-2-oxabicyclo[4.4.0]decane). At the same time, as a corresponding perfluorocarboxylic fluoride, there was simultaneously obtained 6.5 g of perfluoro(2-methyl-3-cyclohexylpropionyl fluoride).

EXAMPLE 3

In the same electrolytic cell as used in Example 1, the electrolytic fluorination was carried out under the same reaction conditions by following the same procedure as in Example 1, except that 2-methyl-3-cyclohexylpropionic acid (0.141 mol) for 185 Ahrs until the electrolytic voltage reached 8.0 V.

After the completion of the electrolysis, the drain cock at the bottom of the electrolytic cell was opened to discharge 32.3 g of a mixture of fluorocarbons.

In the cooled trap, there was obtained 3.1 g of a mixture of fluorocarbons. The two mixtures were put together and subjected to the same treatment and analysis as involved in Example 1. Consequently, there was obtained 4.3 g (6.4% of yield) of a product identified to be perfluoro(4-methyl-2-oxabicyclo[4.4.0]decane). At the same time, as a corresponding perfluorocarboxylic fluoride, there was simultaneously obtained 2.0 g of perfluoro(2-methyl-3-cyclohexylpropionyl fluoride).

1. Perfluoro(4-methyl-2-oxabicyclo[4.4.0]decane) represented by the structural formula:
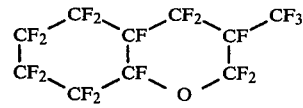

What is claimed is: